(12) United States Patent
Saini (10) Patent No.: US 9,903,844 B2
(45) Date of Patent: *Feb. 27, 2018

(54) TECHNIQUES FOR DETERMINATION OF HALOACETIC ACID ("HAA") PRESENCE IN AQUEOUS SOLUTION

(71) Applicant: AMS Trace Metals, Inc., Sunnyvale, CA (US)

(72) Inventor: Harmesh K. Saini, Santa Clara, CA (US)

(73) Assignee: AMS Trace Metals, Inc., Wilmington, DE (US)

( * ) Notice: Subject to any disclaimer, the term of this patent is extended or adjusted under 35 U.S.C. 154(b) by 110 days.

This patent is subject to a terminal disclaimer.

(21) Appl. No.: 14/944,836

(22) Filed: Nov. 18, 2015

(65) Prior Publication Data

US 2016/0169847 A1 Jun. 16, 2016

Related U.S. Application Data

(63) Continuation of application No. 14/116,764, filed as application No. PCT/US2012/036840 on May 7, 2012, now Pat. No. 9,222,921.

(60) Provisional application No. 61/487,653, filed on May 18, 2011.

(51) Int. Cl.
| | | |
|---|---|---|
| G01N 30/74 | (2006.01) | |
| G01N 30/02 | (2006.01) | |
| G01N 30/88 | (2006.01) | |
| G01N 31/22 | (2006.01) | |
| B01L 3/00 | (2006.01) | |
| G01N 33/18 | (2006.01) | |

(52) U.S. Cl.
CPC ............ *G01N 30/74* (2013.01); *G01N 30/02* (2013.01); *G01N 30/88* (2013.01); *G01N 33/1826* (2013.01); *G01N 2030/8845* (2013.01); *Y10T 436/193333* (2015.01); *Y10T 436/196666* (2015.01)

(58) Field of Classification Search
CPC ........ G01N 30/74; G01N 30/02; G01N 30/88; G01N 1/405; G01N 33/54366; G01N 31/223; G01N 31/22; G01N 31/02; B01L 2400/0406; B01L 3/5023; B01L 3/502; B01L 3/50
USPC ........ 436/125, 124, 178, 177, 174; 422/416, 422/405, 402, 400, 69, 68.1
See application file for complete search history.

(56) References Cited

U.S. PATENT DOCUMENTS

| | | |
|---|---|---|
| 5,547,877 A | 8/1996 | Friedman |
| 9,134,290 B2 | 9/2015 | Saini et al. |
| 2003/0092196 A1 | 5/2003 | Saini |
| 2010/0204924 A1 | 8/2010 | Wolfe et al. |

FOREIGN PATENT DOCUMENTS

WO  WO2011133383 A2  10/2011

OTHER PUBLICATIONS

Wang et al, Continuous, on-line monitoring of haloacetic acids via membrane extraction, Journal of Chromatography A, 1089 (2005), 39-44. (Year: 2005).*
Carrero et al, Analysis of haloacetic acid mixtures by HPLC using an electrochemical detector coated with a surfactant nation film, Talanta, 48 (1999) 711-718. (Year: 1999).*
Esp@cenet English abstract of Chinese Application No. CN20111398607 for Method for quickly detecting haloacetic acids serving as disinfection byproducts in drinking water, Jun. 27, 2012.
Esp@cenet English abstract of Japanese Application No. JP2013092520 (A) for Measurement Method and Measurement Device for Haloacetic Acid, May 16, 2013.
Wang et al., "Microfluidic Supported Liquid Membrane Extraction," Alalytica Chimica Acta. 543 (2005) 92-98.
Carrero, "Analysis of Haloacetic Acid Mixtures by HPLC Using an Electrochemical Detector Coated With a Surfactant Film," Talanta, 1999, pp. 711-718.
Dionix, Acclaim Polar Advantage HPLC Columns, 2003, pp. 1-8.
ISR/WO, PCT Patent Application PCT/US12/36840, dated Nov. 23, 2012, pp. 1-12 (issued in the parent case to this application).
Kou, D. et al., Journal of Chromatography A., 2004, v. 1055, pp. 63-69.
Sohn, J. et al., Environmental Engineering Research, 2007, vol. 12, pp. 224-230.

* cited by examiner

*Primary Examiner* — Christine T Mui
(74) *Attorney, Agent, or Firm* — Marc P. Schuyler (57) ABSTRACT

A real-time method and analytical system for determining haloacetic acids in water which operate by: (1) extracting samples on ion-exchange absorbent medium; (2) concentrating haloacetic acids on hyper-crosslinked medium; (3) eluting the analytes from the concentration medium for injection into an HPLC system; (4) separating individual haloacetic acid in reverse-phase chromatography performed by the HPLC system; and (5) measuring optical characteristics (UV-absorbance) of haloacetic acids, to determine concentration. The entire process can be performed using a completely self-contained, in-situ mechanism that sits at a water distribution point for 24/7 testing, with automated control, monitoring, reporting, and employment of remedial measures (e.g., automated adjustment of the water treatment process).

21 Claims, 5 Drawing Sheets

TECHNIQUES FOR DETERMINATION OF HALOACETIC ACID ("HAA") PRESENCE IN AQUEOUS SOLUTION

This application is a continuation of U.S. Utility patent application Ser. No. 14/116,764, filed Nov. 9, 2013 as a national stage entry under 35 USC § 371 of PCT Patent Application PCT/US12/36840, filed May 7, 2012, issued on Dec. 29, 2015 as U.S. Pat. No. 9,222,921. The aforementioned applications also claim the benefit of U.S. Provisional Patent Application No. 61/487,653, filed May 18, 2011. Each of the aforementioned patent applications has a first-named behalf of inventor Harmesh K. Saini, and is entitled "METHOD AND APPARATUS FOR DETERMINATION OF HALOACETIC ACID ("HAA") PRESENCE IN AQUEOUS SOLUTIONS." This disclosure is also related to PCT Patent Application PCT/US11/32438 for "Methods and Apparatus for Determination of HaloHydrocarbons in Water," filed on Apr. 14, 2011 (issued on Sep. 15, 2015 as U.S. Pat. No. 9,134,290). This earlier PCT Patent Application provides methods and devices for detection and control of different types of disinfection by-products (DBPs) that, in concert with the teachings of this disclosure, provide powerful solutions for effectively testing for harmful substances in solution (e.g., potable water). Each of the aforementioned patent applications is hereby incorporated by reference, as though identically set forth herein.

This disclosure relates to measurement of haloacetic acids in aqueous solutions. More particularly, this document provides methods and devices that can be used for automated and/or remote measurement of haloacetic acids (HAAs) in water, based upon ultraviolet ("UV") absorbance detection and the use of liquid chromatography (LC).

BACKGROUND

The water industry is facing many challenges, one of which is the understanding and control of disinfection by-products (DBPs). The negative effects of DBPs on public health and the environment have raised concern over the use of these compounds; the presence of these compounds in a water supply is now strictly regulated in many countries. The DBPs have been found to be carcinogenic, mutagenic, hepatoxic and to cause adverse reproductive and developmental effects in human beings.

Haloacetic acids (HAAs) are one of the main DPBs that have been identified in chlorinated water. HAAs are considered to be hazardous to humans at high concentrations and prolonged exposure, and maximum regulatory limits for HAAs have been established in a number of industrialized countries. The primary HAAs formed during chlorination are monochloroacetic acid (MCAA), dichloroacetic acid (DCAA), trichloroacetic acid (TCAA), monobromoacetic acid (MBAA), dibromoacetic acid (DBAA), tribromoacetic acid (TBAA), bromochloroacetic acid (BCAA), chlorodibromoacetic acid (CDBA) and bromodichloroacetic acid (BDCAA). The first five of these are the most common, and are regulated under the US Environmental Protection Agency's Disinfectants/Disinfection by-products (D/DBPs) rule with a maximum aggregate contaminant level of 60 µg/l. The World Health Organization has been more specific by setting individual limits for DCAA (50 µg/l) and TCAA (100 µg/l).

Unfortunately, chlorine remains an important disinfectant worldwide, as it provides residual disinfection capability within water supplies. As a consequence, the use of chlorine to disinfect water is considered to some extent a necessary evil, and it is important to monitor the presence of HAAs as a DPB, and to correct excessive HAA presence as part of the water distribution process.

Various techniques exist to determine HAA presence in water, generally relying on gas-chromatography, liquid chromatography, ion-chromatography, capillary electrophoresis, electrospray ionization or similar analytical techniques. However, without pre-concentration of HAAs from bulk potable water, most of these techniques cannot reliability and reproducibly achieve required detection limits. Pre-concentration techniques, in turn, are laborious and time consuming, and often require careful process controls that generally are only obtained in a sophisticated laboratory setting. For example, EPA Method 552.2 calls for liquid-solid extraction of HAAs. A sample is adjusted to pH 5.0 and HAAs are then extracted with a preconditioned anion exchange column. Analytes are eluted with small aliquots of acidic methanol and esterified directly in this medium after the addition of methyl-tert-butyl ether (MTBE) as a co-solvent. Methyl esters of HAAs can then be quantified (i.e., as an aggregate measure of HAAs) by gas chromatography (GC) equipped with an electron capture detector (ECD) or a mass-spectrometer (MS).

Thus, in a typical testing process, water samples are typically collected in-situ using vials and then transported to an offsite laboratory for performance of these processes which is to say, these techniques often require significant cost and lead time. Most of the methods and apparatus described in the literature require expensive equipment (with substantial maintenance demands) and extensive personnel training. Also importantly, these techniques often involve direct operator contact with hazardous chemicals and involve significant latencies before problems in a water supply can be detected and corrected.

A need therefore exists for a better process and system for measuring HAAs. More particularly, a definite need exists for HAA measurement techniques which are faster and more accurate, ideally being performed in near-real time. It should be appreciate that with quick turnaround, water supplies can more quickly react to high HAA levels, so as to minimize any public exposure to these harmful substances. Further, a need exists for techniques which avoid excessive direct operator interaction with harmful substances used in the measurement of HAAs. Still more particularly, a solution to these problems could be employed remotely, e.g., with in-situ testing, and with automatic, network based monitoring, detection, correction and reporting. Ideally, such a solution would be relatively low cost, such that it could be readily employed in association with any water supply, e.g., by a local water company at many points of distribution. The present invention satisfies these needs and provides further related, advantages.

SUMMARY OF THE INVENTION

This disclosure provides a low cost, simple, reproducible, in-line, on-line and real-time method and apparatus to measure haloacetic acids (HAAs) in an aqueous solution. More particularly, this disclosure provides a process and system for measuring HAA presence that relies on UV absorbance techniques. These techniques can optionally be implemented in an in-situ mechanism that provides automated water sample extraction and HAA pre-concentration, and that provides localized processing using a built-in liquid chromatography (LC) system and localized UV analysis. Optionally, such a mechanism also includes a control mechanism that permits remote water testing and monitoring, e.g., such that control can be automated and provided from a remote facility 24/7, without requiring on-site continuous human management.

In more specific implementations, the disclosed techniques are optionally based upon an improved HAAs extraction and concentration method and subsequent separation by reverse-phase high-performance-liquid-chromatography (HPLC) and detection by UV-absorbance. In this detailed optional embodiment, extraction is performed using by anion ion-exchange methodology at pH>7, where the HAAs are fully deprotonated as negatively charged ions. During extraction, a water sample is passed through an anion ion-exchange polymer with positively charged functional groups. The polymer adsorbs negatively charged HAAs along with other negatively charged species in the water sample. After extraction, most of the negatively charged species along with the HAAs are displaced from the anion ion-exchange polymer with a strong acidic solution with pH<1, an ion-displacement solution, on to a hyper-cross-linked polystyrene-type polymer. At this low pH, the HAAs are fully protonated with double bonds ($\pi$ electrons) >C=O. The hyper-crosslinked material selectively retains HAAs as a function of the $\pi$-$\pi$ interaction. This technique helps eliminate the need of liquid-liquid or liquid-solid phase extraction as required by gas chromatograph ("GC") or other analytical methods.

Another benefit of this more detailed embodiment is optionally providing an improved reverse-phase chromatographic method with UV-absorbance detection. Deep UV-absorbance in the range 180 nm to 220 nm is very selective for small species, such as HAAs with double bonds. At this UV-absorbance range other organic species are filtered out and the risks of interferences from other organic matters in the sample are minimized. By optimizing the chromatographic conditions, the time-based separation of all nine HAAs can be controlled. A method is disclosed whereby the individual concentrations of all nine HAAs in a potable water sample can be determined, enabling sophisticated controls, monitoring, diagnostics, alarms and other processes.

Further aspects of the invention provide a device that can be installed in-situ to periodically and automatically measure HAAs presence in a test sample, for example, a municipal water supply. The results can be automatically logged into a database for monitoring, compliance or other purposes, and can be transmitted if desired over a network (such as the internet) to a central control or reporting station, for example, that monitors multiple such devices.

Further benefits will become clear from the description below.

DETAILED DESCRIPTION

This disclosure provides (a) a process and system for measuring HAA presence that relies on UV absorbance techniques; (b) an in-situ mechanism that provides automated water sample extraction and HAA concentration (optionally, this mechanism can also be integrated with the UV absorbance process and LC system, such that measurement and/or calculation is also performed in-situ); (c) a control mechanism that permits remote water testing and monitoring, e.g., such that control can be automated and provided from a remote facility 24/7, without requiring on-site continuous human management; and (d) business methods relating to testing, reporting and oversight based on these principles. Other advantages will also become apparent from the disclosure below.

As mentioned, one embodiment provided by this disclosure is a process for extracting and measuring haloacetic acids (HAAs). The process can be performed generally in four steps: 1) extracting a sample containing analytes of interest and passing the sample over a porous adsorbent surface; 2) recovering extracted analytes from the adsorbent surface and transferring the extracted analytes onto another polymer for concentration; 3) introducing concentrated, extracted analytes to a liquid chromatography (LC) system for separation; and 4) measuring HAA presence via UV absorbance. This process is optionally performed by an in-situ mechanism, in a laboratory, or using other techniques.

A second embodiment provides an in-situ mechanism that performs some or all of the steps or mechanisms just identified. The in-situ mechanism performs localize sample extraction and sample concentration for purpose of testing. In a more detailed embodiment, the in-situ mechanism also provides for localized separation and chromatographic analysis, and digitization of results. The in-situ mechanism in one more detailed embodiment includes mechanisms for calibration and standardization, providing for accurate results, normalized against known samples. An on-board LC system with automated control is optionally used for this purpose. The digitized results are processed by on-board logic, or they can be transmitted via a local or wide area network (e.g., a LAN or a WAN such as the Internet) to a remote computer for analysis.

Optionally employed together, the methods and in-situ mechanism provide for automated monitoring and compliance, with real-time feedback to ensure maintenance of safe HAA levels, and with logging to ensure greater accountability. Other benefits and advantages will become apparent from the description below. Note that although the measurement of HAA concentration in water is a principle end of this disclosure, the techniques provided by this disclosure are extendable to other aqueous media; that is to say, the term "water" should be understood to refer to potentially any aqueous media and not necessarily limited to potable water.

The measurement of HAAs can be important in many contexts, among them regulation of a potable water supply.

As noted, the embodiments presented in this disclosure facilitate a device and related method that can be used by or for a local water company or municipal water supply for in-situ measurement of HAAs, that is, without requiring special personnel training or experience normally associated with manual field usage of a mass-spectrometer or electron-capture detector or other sophisticated equipment. Through the use of a liquid-solid phase extraction and concentration, the embodiments presented herein provide a system that can be repeatedly cycled with little maintenance and with reduced exposure to noxious fumes and hazardous chemicals and with relatively greater accuracy and reliability. As the embodiments presented herein can be used in-situ, under control of an electronic control system (e.g., a computer), these embodiments facilitate (a) a remote monitoring system (e.g., via a local area network or "LAN," or over the internet, with results reported to a central monitoring system), and (b) consequent greater accuracy and improved data retention for compliance and monitoring purposes.

Figure 1:
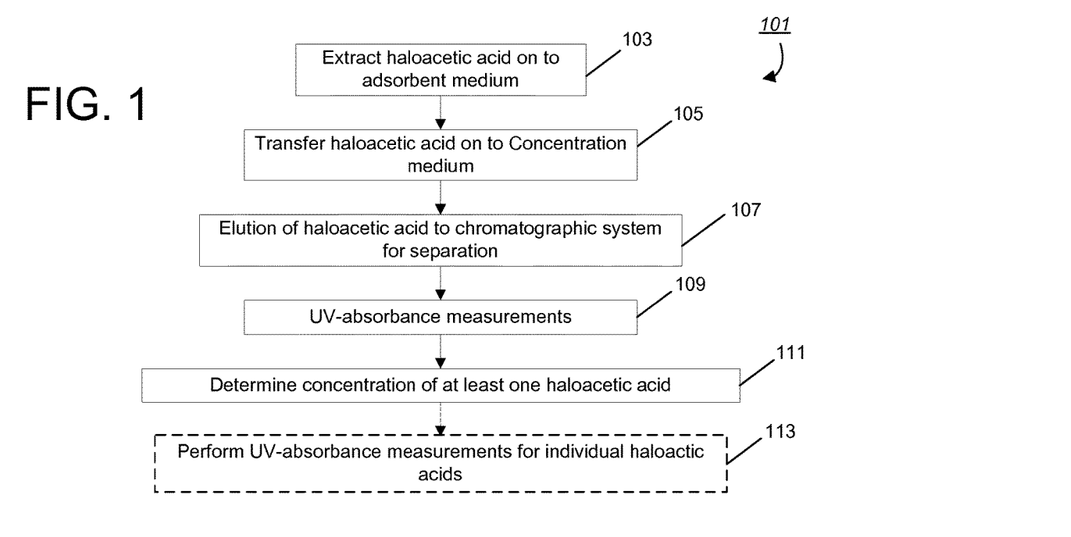
FIG. 1 provides a block diagram of a process 101 for extracting and/or measuring haloacetic acids (HAAs) based on UV absorption.

FIG. 1 provides a block diagram of an embodiment 101 of a method and system for measuring HAAs. A sample is first processed to extract at least one haloacetic acid to an adsorbent medium, as indicated by step 103. After being extracted on the adsorbent medium, the haloacetic acid is transferred to a concentration medium, as referenced by numeral 105. The analytes are eluted from the concentration medium and introduced into a chromatography system for separation, as indicated by step 107. This system is optionally a high-performance liquid chromatography system, as indicated by the acronym "HPLC." As depicted by reference numeral 109, the separated HAAs are measured by exposing an extracted, concentrated sample to ultraviolet (UV) radiation, and by determining UV-absorbance using an optical spectrometer. Based on the measured absorbance results, haloacetic acid concentration is determined, as indicated by reference numeral 111.

In fact, there may be several HAAs present in unknown quantities, and the system of FIG. 1 is therefore optionally applied to discriminate between the HAAs and to determine their individual concentrations. As indicated by dashed-line (i.e., optional) process block 113, the UV absorbance peaks are individually discriminated to differentiate multiple HAA species.

As will be presented below, based upon predetermined data, total HAAs presence as well as individual HAA concentrations can be determined from this data based on an in-situ mechanism, leading to real-time measurements and results. Computations leading to these results, and any resultant action, can be controlled locally, or can be directed to and controlled by a remote computer or monitoring station.

Figure 2:
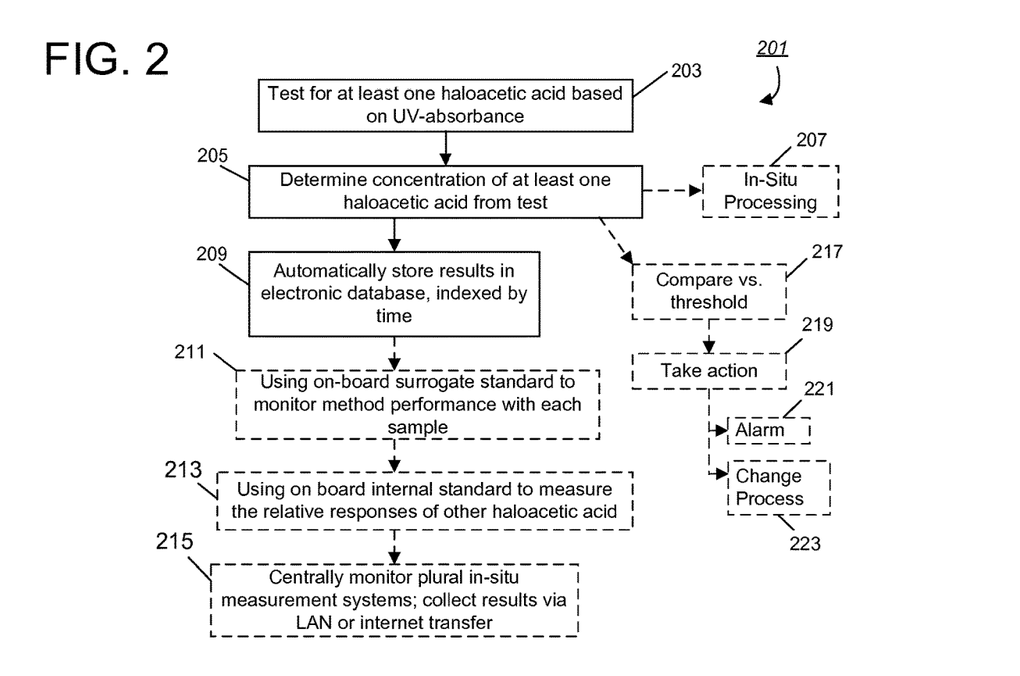
FIG. 2 provides a block diagram of a process 201 of monitoring for HAA presence. As represented by dashed lines, the embodiment optionally features in-situ processing and measurement of relative response of other HAAs present; alternatively or in addition, such measurement is optionally part of a remote monitoring system that monitors a network of several such mechanisms.

FIG. 2 introduces another embodiment 201 of an HAA measurement process; FIG. 2 is also used to introduce concepts of related business methods.

In particular, as represented by function block 203, a water sample is collected and testing is performed to determine HAA presence based on UV absorbance. From this testing, the presence of one or more HAAs is determined, per block 205. This determination is optionally performed to determine a HAA aggregate concentration (e.g., of the HAA5, described earlier) or to determine presence of individual HAA species. In terms of "presence," these determinations are performed to either make relativistic determinations (e.g., by comparing presence against a threshold, e.g., "zero"), or by determining concentration, in relative or absolute terms; other bases are also possible. As represented by dashed-line function block 207, testing is optionally performed in-situ; for example, in one envisioned implementation, the in-situ mechanism includes a local UV-absorbance detection mechanism, for example, relying on local chromatographic separation and measurement. Such a local unit can be made entirely self-contained, that is, with water sample extraction and extraction chemical introduction being entirely automated, to help limit worker exposure to noxious fumes or hazardous chemicals. Algorithmic processing to determine specific HAA percentages is then performed locally, or alternatively, by a remote computer (e.g., such as at a central station for the water supply, by a regulatory agency, or by a third party hired for remote testing). The results can be electronically stored in a database, indexed by time, thereby serving the compliance goals referenced above, e.g., a log may be generated and kept to show compliance and to track situations and times when detected substances exceed desired levels, as alluded to by numeral 209.

Note that one embodiment of an in-situ mechanism (to be discussed further below) provides for modular supply chemical replacement, with completely automated "on-line" sample extraction, localized concentration and measurement, and network-based reporting of results, process cycle and alerts (e.g., indicating need for periodic maintenance). That is to say, the use of the techniques as taught by this disclosure facilitates local, relatively easy maintenance; the materials used for the regeneration of the extraction column and conditioning of the concentration column may be stored in local, modular reservoirs and occasionally replenished, with spent chemicals also being modularly collected for safe disposal. Such an automated mechanism provides for easy maintenance without requiring extensive training of personnel.

FIG. 2 also illustrates several other dashed-line function blocks, relating to the way testing is optionally controlled and the manner in which remedial action is optionally taken. First, for embodiments that use computer control of the various sampling and testing steps, a LAN or a WAN (e.g., an Internet connection) may also be provided for transmitting measurement results to a central monitoring facilities, e.g., a regulatory agency, regional water management station, or some other type of entity, thereby providing for enhanced ability to continuously monitor chemical levels and quickly respond to problems. Any or all of the elements of testing, computing, monitoring, logging, or taking remedial action can be combined together in a single machine, or distributed in a diverse manner across a local or wide area network.

Function block 211 indicates that an on-board control device can be integrated with the in-situ mechanism to perform certain functions, for example, the normalization or calibration of local equipment using an on-board surrogate standard. Per function block 213, internal standards can also be used in direct comparison with live water samples, that is, to provide relative responses that compare measured (i.e., variable) HAA presence to norms established by the local standard. As indicated by numeral 215, data from any one or more in-situ mechanisms can be centrally or remotely monitored, with data from a particular in-situ machine indexed by various factors, including time of measurement, particular HAA values, an identifier of the particular machine that produced the data, location, etc. Once again, this data may be logged either in a dedicated file, or as part of a database used to track several of the in-situ mechanisms.

Possible remedial actions are indicated by the right side of FIG. 2. That is to say, measured HAA levels (either in the aggregate or specific to acid species) are optionally compared with one or more thresholds, per numeral 217. An alarm is generated if HAA concentrations exceed desired level, for example, in the form of an audible signal, an alert email, a visual indicator, or some other mechanism; alternatively, an electronic control system may responsively and automatically adjust upstream water treatment processes, either by increasing or decreasing the use of certain chemicals, to provide for a sanitized water supply without exceeding recommended HAA norms. Individual HAA species contributions are also optionally used in diagnosing issues associated with the water treatment process. These principles are variously represented by numerals 219, 221 and 223 in FIG. 2.

With several principal features of the present disclosure thus introduced, additional detail will now be presented, with reference to FIGS. 3-6.

Figure 3:
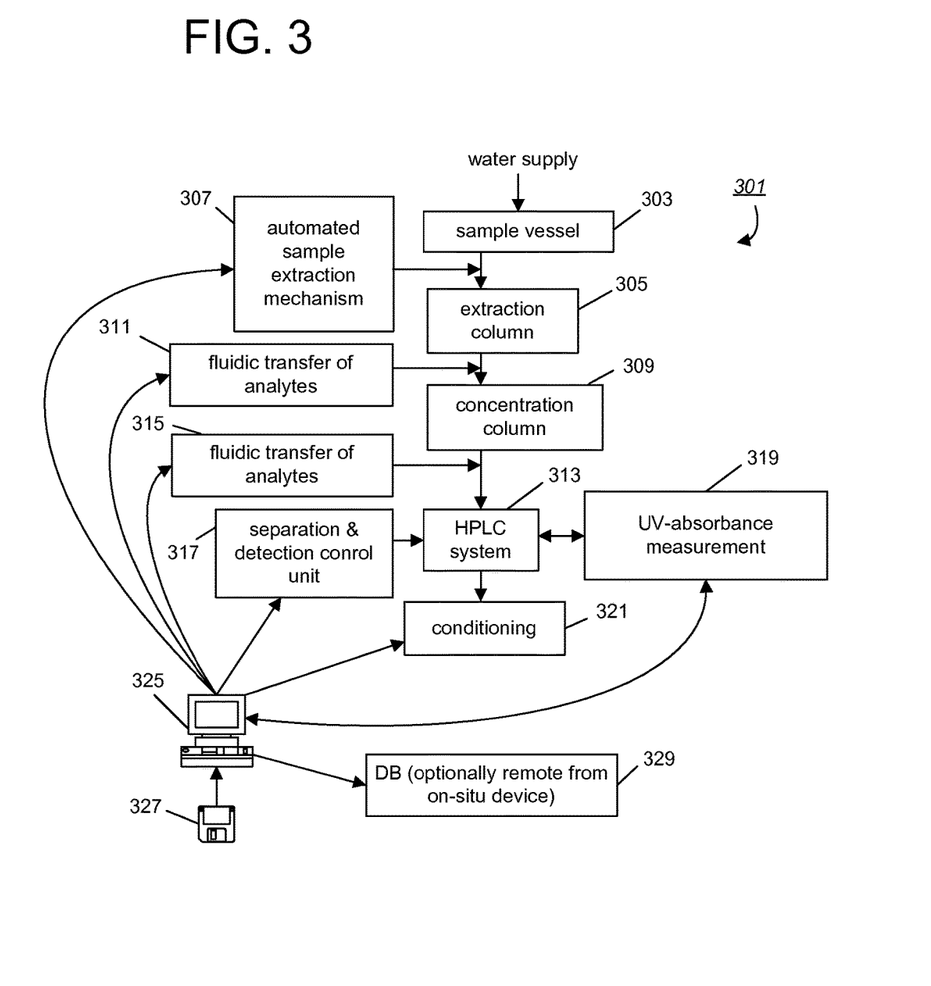
FIG. 3 provides a block diagram of an embodiment 301 of a system or device for measuring HAAs.

FIG. 3 presents a block diagram of an embodiment 301 of a system for measurement of HAAs. In an example context, a potable water supply is to be monitored to periodically determine the presence of HAAs. In one embodiment, monitoring may occur at frequent intervals, for example, every two hours, around the clock. The water supply may be (for example) a particular point in a municipality's or water company's distribution network. At each monitoring interval, a sample is extracted from the potable water supply and transferred to a vessel 303. The sample extraction may be part of an in-situ mechanism that automatically draws a predetermined volume of water into the sample vessel. HAAs are then extracted from the water test sample using an extraction column, per numeral 305. This column contains an adsorbent medium as previously introduced (e.g., a hyper-crosslinked polystyrene medium), with extraction being accomplished by passing the water test sample through, and adsorbing the analytes to the adsorbent medium. Both the drawing of the water sample and transference to the adsorbent medium can be performed under the governance of an automated mechanism, as alluded to be reference numeral 307. For example, this mechanism can consist of software or firmware that drives electromechanical actuators to draw the water sample via syringe, with automated transfer to the extraction column (a more detailed understanding of such a mechanism is presented below). Once the extraction is complete, the now-extracted analytes are transferred to a pre-concentration medium, per numeral 309, under the control of a fluidic transfer control process 311. This process 311 flushes analytes from the pre-concentration medium for provision to the HPLC system 313 for separation. The HAAs are then separated using a reverse-phase HPLC column 313. The separation mechanism in this reverse-phase column is facilitated by hydrophobic binding between the HAA molecules with in mobile phase and molecules in stationary phase, and is performed under the control of a suitable fluidic transfer process 315. Once again, this process can be driven by firmware or other instructional logic that controls electromechanical actuators to drive fluidics transfer processes. The differences in retention times of each HAAs molecule in the HPLC column 313 result in individual HAA separation. Under the governance of another control process (separation and detection) 317, the separated HAA components are then individually passed through ultra-violet (UV) absorbance measurement system 319. A detector within this system absorbs light in the range 180 to 220 nm, which responses to each HAA with a peak (chromatographic signal); the area associated with each peak is used to determine concentration of each HAA species.

FIG. 3 also illustrates a computer or other suitable machine 325, control software 327, and a number of control arrows to show that the computer is used in this embodiment to provide electronic control for automating the steps (and associated timing) of each of the elements referred to above. For example, such a computer or other machine can be used to control conditioning and transfer processes for the HPLC system and for UV measurement, per numeral 321, and can also be used to mathematically compute HAA concentration using data provided by the UV absorbance measurement system 319. As noted, the computer can be controlled according to a predetermined time schedule or remotely, on a dynamic basis, to automatically perform testing steps from test sample extraction, to HAA calculation, without human intervention. If desired, UV absorbance test results can also be relayed to a remote location, with HAA concentration calculation being remotely performed and with remove maintenance of a database showing results history, per numeral 329.

As indicated, one feature of embodiments presented in this disclosure is the use of a modified extraction and concentration of HAAs to overcome the deficiencies of the basic chemical derivitization of HAAs for GC methods, based on the use of liquid chromatography and optional individual species separation. Such a system can be implemented purely or partially as an in-situ mechanism with localized control per the various functional blocks of FIG. 3. That is to say, all of these elements are optionally integrated together in a single housing, with fluidics control, a sample extraction column and concentration column, a HPLC system and a UV absorption system.

More detailed information about the chemical processing optionally performed by the embodiment of FIG. 3 is as follows:
- the system extracts anionic species, including HAAs, from bulk sample volume, e.g., from the potable water supply;
- the system then concentrates these species onto an hyper-crosslinked material, enhancing sensitivity, reducing bias and eliminate interferences—in one embodiment, the anionic species are by this process continuously adsorbed on a porous surface of anion ion-exchange polymer;
- the species are then quantitatively desorbed from the hyper-crosslinked material by a stripper solution; the species are then separated by reverse-phase chromatography; and
- measurements are then made through the UV-absorption to determine HAA concentrations based on what was extracted from the sample volume.

These tasks can be performed such that the entire measurement takes less than two hours, i.e., with periodic, repeated testing, fully automated if desired, being performed under the auspices of a computer control, twenty-four hours per day, seven days per week (24/7).

Figure 4:
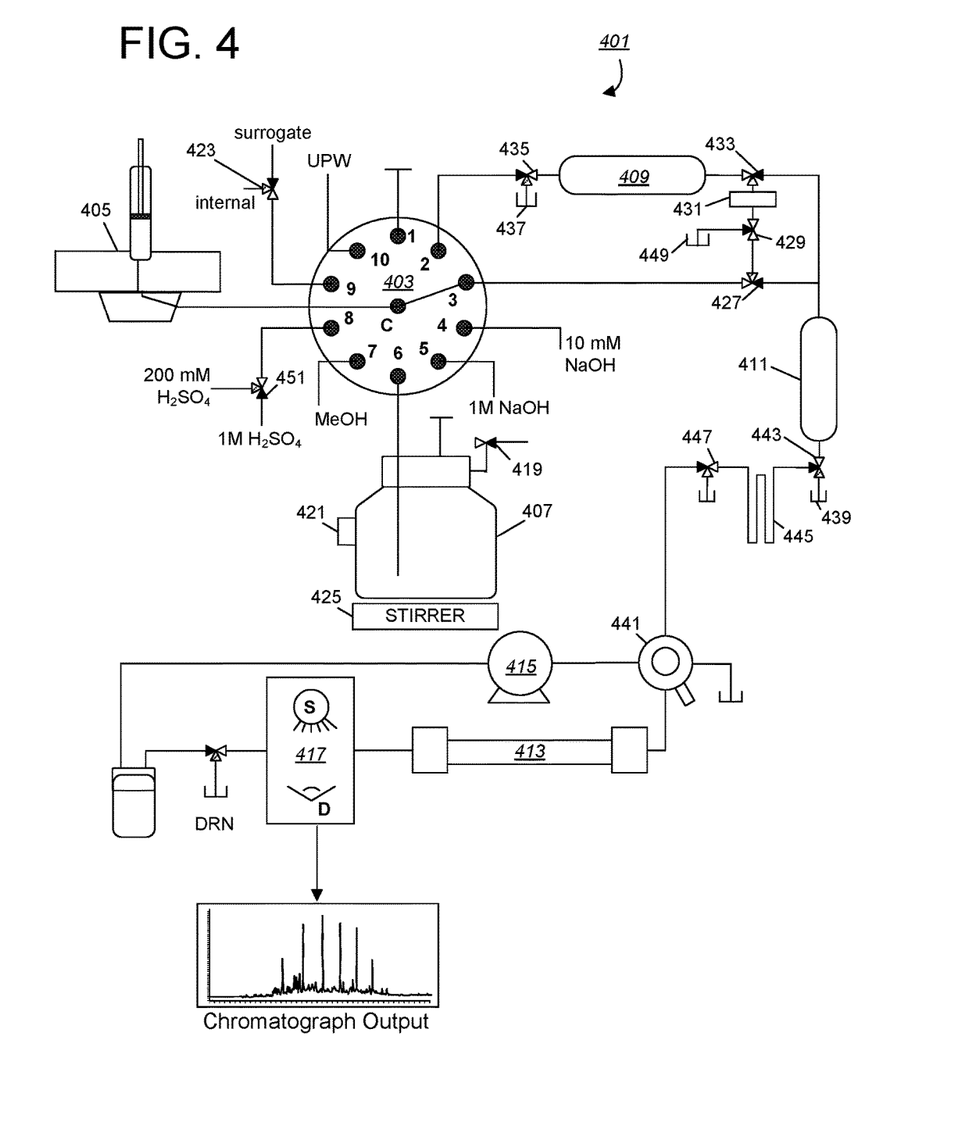
FIG. 4 provides a schematic 401 of an in-situ device for measuring HAAs, for example, a device for automatically extracting water samples and processing these samples in-situ to determine HAAs presence in potable water, on a real time basis.

FIG. 4 is a schematic of another embodiment of an analytical system 401 in which HAAs are extracted on a porous adsorbent material and concentrated on another hyper-crosslinked material. To first provide a high-level description of several elements of FIG. 4, a rotary selector value 403 and a syringe mechanism 405 are used to transfer fluids through different parts of the system. For example, the drawing of the initial water sample, the passing of this sample over an adsorbent column, the transfer of fluidics to HPLC/UV systems, and purging and calibration, are all controlled using these central elements, again, acting under electromechanical actuation by a computer running appropriate software (e.g., firmware or other instructional logic, not seen in FIG. 4). The rotary selector value 403 has a number of ports (i.e., ports 1-10 and center tap "C") which are used to multiplex the various sources and destinations of fluids within the system 401. At a high level, a water sample is drawn into a sample vessel 407, seen in the approximate middle of FIG. 4, just below the rotary selector valve 403. The extraction column, labeled 409, is seen at the upper right of FIG. 4, and the concentration column 411 is seen at the far right of FIG. 4. The HPLC is seen as a collection of elements at the bottom of FIG. 4, including a reverse-phase HPLC column 413, and a HPLC pump 415. The UV detector is also seen at the bottom of FIG. 4 and is labeled 417.

During operation, water enters the sample vessel 407 via a two-way valve 419; the sample amount is predetermined depending upon the required detection limit and historic makeup of the sample, with amount being controlled by an optical sensor 421. An internal standard and a surrogate standard, each of known concentration, are also added to the sample through port-9 of rotary selector valve 403, via three-way control valve 423. The syringe mechanism 405 pushes the internal standard and surrogate standard to the sample vessel 407. A stirrer plate 425 then mixes the water sample with the added standards. After about 2-3 minutes of mixing, the stirring stops and the syringe mechanism 405 pulls the mixed sample through port-6 of the rotary selector valve 403 and pushes it through port-3 onto the previously regenerated (i.e., cleaned) extraction column 409; as mentioned, this extraction column is packed with porous ion-exchange adsorbent material. This material can advantageously be formed from a polystyrene-divinylbenzene based polymer providing weak anion ion-exchange with tertiary or secondary amine functional group, such as via DEAE (diethylaminoethyl) or providing strong anion exchange functionality, for example, using trialkylbenzyl ammonium (Amberlite, USA) or trimethylbenzyl ammonium (Dowex Type I), or dimethyl-2-hydroxyethylbenzyl ammonium (Amberlite, Dowex Type II, USA), or dimethylethanolbenzyl ammonium (Dowex Type II). Other materials may of course be used. The sample is passed through three-way valves 427 and 429, a sub-micron filter 431 (e.g., 0.2 or 0.45 microns) and then through three-way valve 433. The filter 429 retains any particulate from the sample. After passing through the extraction column 409 with the HAAs being continuously adsorbed, remaining fluid is drained out through three-way valve 435 to drain 437, as waste; the drain 437 leads to a secure disposal container which may be periodically removed as a module from system 401 as a module and securely disposed of. The flow of the sample through the extraction column could vary from 0.5 ml per minute to 4 ml per minute. Some other anionic inorganic and organic species may also be adsorbed as part of that process to the extraction column.

After HAAs (along with some interfering anionic organic and inorganic species) are extracted onto column 409, they are displaced from ion-exchange material of the extraction column with an ion-displacer solution (1M $H_2SO_4$), via port-8 of the rotary selector valve 403. Ions in the displacer solution (e.g. $SO_4^{-2}$, $Cl^{-1}$, $NO_3^{-1}$) with a high affinity to the anion ion-exchange matrix will compete effectively for binding sites on the column with HAAs and other anionic ions, and thus displace all molecules with lesser affinities such as HAAs into the solution. A predetermined volume of the displacer solution is pushed through the extraction column 409 and into the pre-concentration column 411. HAAs are retained by the pre-concentration column 411 while the other anionic species are passed through to a drain 439. The selective retention of HAAs onto the pre-concentration column 411 is attributed to the specific π-π bond interaction between HAAs (carboxylic moieties) with hyper-crosslinked polystyrene material packed in column 411. The hyper-crosslinked material in column 411 can be selected to include a commercially-available polymer such as "Purosep 200," "Purosep 270" ("Purolite UK"), "LiChrolut EN" (Merck, USA), "Isolute ENV+" (IST, UK) or "StrataX" (Phenomenex, USA). Other materials may also be used.

A small quantity (100 μL to 1000 μL) of stripper solution (NaOH) is then pulled from port-4 of the rotary selector value 403 and into the syringe mechanism 405. The stripper solution is pushed from the syringe mechanism via port-3 of the rotary selector value through the pre-concentration column 411 to an injection value 441 seen at the bottom right of FIG. 4. As part of this process, the stripper solution passes through valves 427 and 443, a 50 uL loop 445 and valve 447. The stripper solution is used to transfer extracted materials to the HPLC system, with the injection valve then serving as the load port for this system.

The detailed operation of reverse-phase HPLC equipped with UV-absorbance detection is omitted for simplicity in description, and is well-understood by those having experience in analytics. At the injection valve 441, 50 microliters of the stripper solution containing concentrated HAAs is injected, with HPLC pump 415 pushing the mobile phase continuously through the HPLC analytical column 413, where individual HAA species are separated. The reverse-phase HPLC column is packed with hydrophobic ligands, chemically grafted to a porous, insoluble matrix (i.e. the stationary phase). The base matrix for a commercially available reverse-phase media is generally composed of silica or a synthetic polymer like polystyrene. In one embodiment, the HPLC column is packed with a porous insoluble silica based polar-enhanced matrix having sulfonomide groups. The separation mechanism in reverse-phase chromatography depends on the hydrophobic binding interaction between the HAAs molecules with the mobile phase and the stationary phase; the differences in retention times of each HAA molecules in the HPLC analytic column 413 result in individual HAA separation. The separated individual HAAs are then passed through the ultra-violet absorbance detector 417. HAAs have double bonds (π electrons) >C=O that absorb UV light in the range of 180 to 220 nm. The sensor of a UV detector consists of a short cylindrical cell having a capacity between 1 and 10 microliters. The mobile phase coming from the HPLC column carries individual HAA through the UV detector cell. Within the detector cell, UV light is arranged to pass through the cell and fall on a photo-electric cell (or detector array). The output from the photocell is passed to an amplifier and then to a recorder or data acquisition system. Finally, the relationship between the intensity of UV light transmitted through a cell and the concentrations of HAAs is given through the application of Beer's Law. In one embodiment, the mobile phase comprises a buffer of approximately 5 mM sodium-dihydrogen-phosphate in approximately 5% acetonitrile, pH-adjusted with hydrochloric acid to approximately 1.0-1.5.

The extraction column 409 is regenerated (i.e., cleaned) before taking the next sample. To regenerate the column, a series of solutions in the following sequence are pushed at different flow rates through the extract column using the syringe mechanism 405 and port-2 of rotary selector valve 403: (1) 10 ml of distilled water from port-10 at 4 mL per minute; (2) 10 mL of 1M NaOH from port-4 at 1 mL per minute; (3) 14 ml of distilled water from port-10 at 4 mL per minute; and (4) 10 mL of air from port-1 at 4 mL per minute. All these solutions pass through three-ways valve 435, extract column 409, three-way valve 433, filter 431 and three-way valve 429 to another drain 449. In this manner, any particulates retained on the filter are also back flushed to the drain and filter is thereby cleaned (purged) for next sample.

The pre-concentration column 411 is also conditioned before the next sample. To effectuate this end, a series of solutions in the following sequence are also pushed at different flow rates through the column 411 using the syringe mechanism 405 and port-3 of the rotary selector valve 403: (1) 4 ml of distilled water from port-10, at 2 mL per minute; (2) 4 mL of air from port-1 at 2 mL per minute; (3) 3 ml of methanol from port-7 at 2 mL per minute; and (4) 3 mL of 200 mM $H_2SO_4$ from port-8 and three-ways valve 451 at 0.4 mL per minute. All these solutions pass through three-way valve 427, pre-concentration column 411, three-way valve 443, en route to drain 439.

Reflecting on the operation of these mechanisms, it is noted that the rotary selector valve 403, the syringe mechanism 405, associated automated control, and supply of the various test and cleaning solutions and standards discussed above, provide for a repeatable process, that is, one that does not require operator involvement at each stage of testing, where solutions and chemicals can be modularly supplied and removed via periodic maintenance. This process also facilitates completely automated testing, calculation of results, with the provision of electronic alerts in the event of problems or when periodic maintenance is needed (such as the emptying or resupply of chemicals). All of these processes can be optionally performed in complete transparency to the on-site workers at a water distribution facility, for example.

The analytical system embodiment just presented has the capability to introduce an internal standard (a pure haloacetic acid of a known amount used to measure the relative response of other HAAs in the sample) and a surrogate standard (a pure haloacetic acid which is extremely unlikely to be found in the sample), with a goal of monitoring method performance. In the case of HAAs determination, the internal standard can be selected to be 2-dichloropropionic acid, 3-diChloropropionic acid, 2,3-dichloropropionic acid or 1,2,3-trichloropropionic acid; other appropriate materials may also be used. The surrogate standard can be selected to be 2,3-dibromopropionic acid, 2-bromopropionic acid or 3-bromopropionic acid or 3,5-Dichlorobenzoic acid, and here also, other alternatives are also possible. To establish relative response measurements, known amounts and concentrations of the internal and surrogate standards are added to the sample vessel 407 by the syringe mechanism 405 and drawn through port-9 of the rotary selector valve, followed by the process described earlier. The UV-absorbances of each HAA are recorded and absorbance values are constructed from the slopes of the concentration vs. absorbance relationships. This calibration slope may be used to quantitatively determine the concentrations of HAAs in previously unknown water samples using the techniques presented above.

As can be seen from this discussion, embodiments presented herein provide a novel, automated way to calculate each individual HAA species of interest, automatically. As alluded to earlier, a control system may, as part of an in-situ device, part of a local area network ("LAN") or as part of a wide area network ("WAN," e.g., the Internet), automatically monitor a water supply and take remedial action, for example, by sounding or otherwise triggering an alarm, or by using an electronic control system and the feedback provided by periodic measurements to adjust chemical treatment upstream in a water sanitation or other process. As also mentioned, the embodiments presented facilitate a device that can be installed in the field near a water distribution system, for the remote (e.g., in-line) collection and analysis of samples, avoiding the need to collect samples in vials and deliver them to an offsite laboratory for analysis. The system may be run continuously, 24 hours per day, unattended, with a warning indication or other action if contaminants exceed a specified limit, responsive to a detected maintenance condition, or on another ad-hoc basis.

Figure 5:
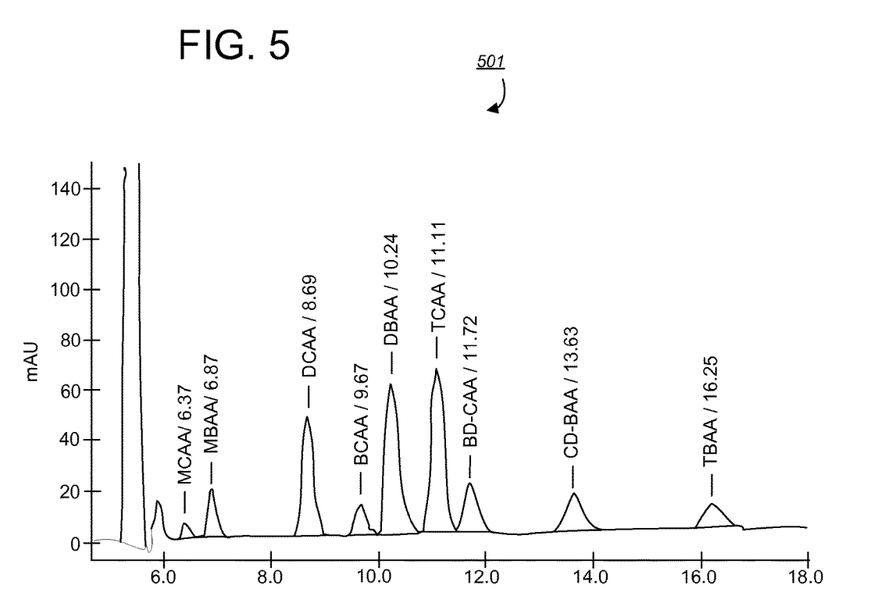
FIG. 5 shows a sample chromatograph 501 used to explain separation of individual HAAs by high-performance liquid chromatography ("HPLC") and concentration determination based upon UV absorbance measurements

FIG. 5 shows a sample chromatogram 501 illustrating analysis of HAAs in the described HPLC system. Each HAA specie is seen to have an associated retention time in the chromatogram, measured by the elapsed time between the moment of injection [time zero] and the time when the peak maximum elutes. By comparing the retention times with that of injected reference standards under the same chromatographic conditions, each HAA can be isolated with its concentration (or alternatively, as part of an aggregate concentration). A series of peaks rising from a baseline is drawn on a time axis. Each peak represents the detector response for a different haloacetic acid. The chromatogram is plotted by the computer data station. The line curves, first upward, and then downward, in proportion to the concentration of the each HAA in the sample band. In this chromatogram all nine HAAs are eluted from the HPLC column in about 17 minutes. To generate the chromatogram of FIG. 5, a Dionex GP 40 HPLC pump 415 is used to push the mobile phase (0.5 mM NaH2PO4 in 5% acetonitrile with adjusted pH at 1.3) at 0.75 mL per minute through a Dionex Acclaim PA column. The UV absorbance for each separated HAA is measured by AD20 absorbance detector from Dionex (i.e., detector 417 from FIG. 4).

Figure 6:
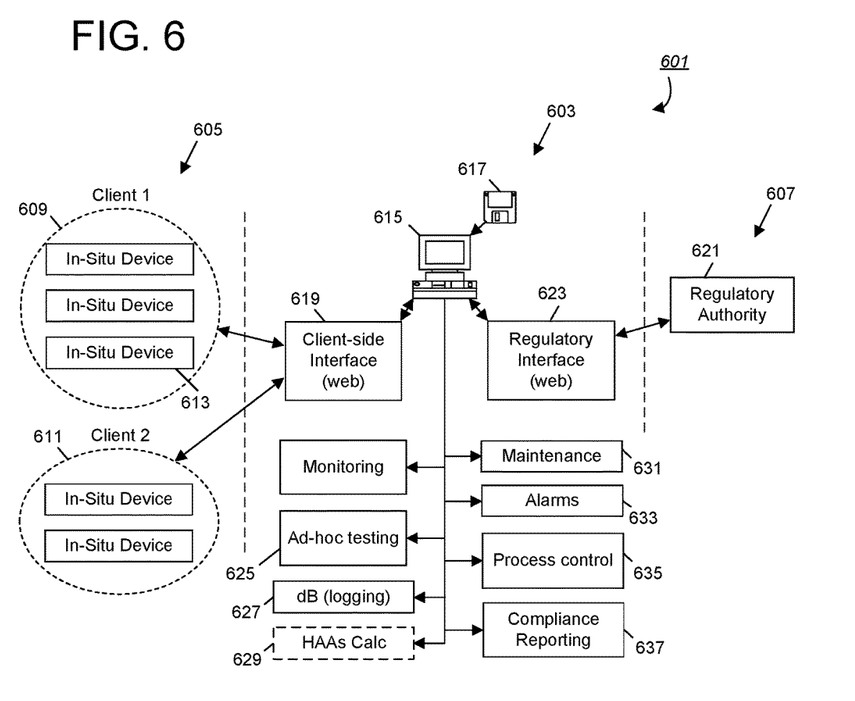
FIG. 6 is a system diagram used to explain a method of remotely monitoring one or more in-situ mechanisms.

FIG. 6 provides a system diagram 601 used to explain a method of remotely monitoring one or more in-situ mechanisms or devices. In particular, FIG. 6 is divided into middle, left and right portions (603, 605 and 607) that respectively represent (a) an on-line or other business that for a fee may automatically monitor one or more water supplies, (b) one or more clients of the business, e.g., one or more municipal water companies, and (c) a regulatory authority or other entity that is to monitor or receive reporting of compliance of any one of the water supplies. Each of these elements is illustrative only, and these methods may be performed only with certain of these entities present; for example, the methods illustrated in FIG. 6 may be performed without interacting with a regulatory authority, i.e., using a private monitoring mechanism internal to a water company or employed via a private party contract.

FIG. 6 in this example illustrates two hypothetical clients 609 and 611, each of which may be taken to be a water company, and each of which may have one or more in-situ devices 613 for monitoring a particular portion of a water delivery network (only one in-situ device is numerically labeled to simplify the illustration). In this regard, it should be assumed that the method (e.g., the business) is to automatically and/or remotely collect measurement data for the purposes of logging HAA data for compliance reporting or other purposes; to this effect, the business 603 includes a supervisory control mechanism 615, depicted as one or more computers running software 617 (e.g., a server system), with this system interfacing both with each client (via a client-side web interface 619), and with a regulatory authority 621 (via a regulatory side interface 623). In one embodiment, the regulatory side web interface may provide a portal for regulatory authorities to remotely audit current and past individual water supply operations, with further ad-hoc tests being initiated as required, and with the business interacting with regulatory authorities on behalf of each client, if desired or appropriate, in a manner transparent to each client. Each interface 619/623 may permit different access levels and present different authentication requirements (e.g., a specific type or level of PKI authentication). For example, because the client side interface may be used for automated communication with each in-situ device 613, each such device may be made to have an embedded cryptographic key for purposes of authentication; on the other hand, because regulatory interaction may involve aggregated, relatively sensitive data, two-factor or other authentication requirements may be used as a predicate for individual access by a remote human user. Regardless of the interface formats, the supervisory system can be configured to perform a number of functions, depicted at the middle of FIG. 6, thereby relieving the clients 609 and 611 from the need to perform these functions themselves, and minimizing the need for on-site presence or inspection by regulatory authorities. As indicated by reference numeral 625, the method may include periodically receiving test data from each one of the plural in-situ devices 613 via the client-side interface 619; each instance of test data may represent an automated process that is initiated by the specific device 613, and/or the supervisory system 615 may also selectively initiate tests. For example, if it is determined that a specific HAA concentration determined from a test is out of normal bounds, an ad hoc test may be commanded by the supervisory control system, as indicated by reference numeral 625. The supervisory control system may perform data base management (627), indexing each set of test data by particular provider, time and date, last known calibration, and any other desired data. As indicated by blocks 631, 633, 635 and 637, the supervisory control system (or a different electronic control system) may also test for and/or respond to maintenance events, generate alarms or take process control actions responsive to comparison of HAA levels against thresholds, and generate automatic compliance reports either for the regulatory authority 621 or a particular client 609 or 611. As further depicted by a dashed-line, optional block 629, if desired, raw data may be reported to the supervisory control system 615, with total and/or individual species HAA calculations being performed by the supervisory control system 615, on a remote basis.

As should be apparent from this description, the methods and devices provided above, by facilitating real-time, relatively same, automated HAA measurement, provide for new advances not only in the measurement process, but also in terms of compliance and accountability, potentially changing the way in which water companies and regulatory authorities do businesses.

Various alternatives to the foregoing techniques will readily occur to those having skill in the art. To pick just a few examples, techniques mentioned above may be applied using other types of detected optical activity (e.g. other than change in UV-absorbance), and haloacetic acid extraction may be accomplished using mechanisms other than an adsorbent medium. To pick another example, the method of business described above may be applied with or without modified extraction and concentration method. Many other variations also exist. Accordingly, the foregoing discussion is intended to be illustrative only; other designs, uses, alternatives, modifications and improvements will also occur to those having skill in the art which are nonetheless within the spirit and scope of the present disclosure, which is limited and defined only by the following claims and equivalents thereto.

I claim:

1. An apparatus for measuring presence of a haloacetic acid ("HAA") in aqueous solution, the apparatus comprising:
   an intake to be fluidically coupled to a supply of the aqueous solution;
   sample extraction mechanism coupled to the intake to draw samples of the aqueous solution from the supply upon electronic actuation, each of the samples having an expected volume;
   an ion separation mechanism to receive each of the samples and to separate negatively charged ions therefrom, the negatively charged ions including the HAA and other ionic species;
   a material to separate the HAA from the other ionic species extracted from each sample;
   a measurement device to measure HAA presence for each associated one of the samples;
   fluid storage to supply at least one fluid;
   at least one transfer mechanism to transfer, upon respective electronic actuation,
      the negatively-charged ions extracted from each sample to the material,
      the separated HAA from the material to the measurement device, wherein the measurement device is to measure HAA presence in the corresponding sample, and
      the at least one fluid to the ion separation mechanism and the material, so as to renew the ion separation mechanism and the material for measurement of an ensuing one of the samples; and
   a control device to electronically actuate each of the sample extraction mechanism, the measurement device and the at least one transfer mechanism to draw each of the samples from the supply, to cause the measurement device to measure HAA extracted from each of the samples using the material and to renew the ion separation mechanism and the material using the at least one fluid supplied by the fluid storage.

2. The apparatus of claim 1, wherein:
   the at least one fluid comprises a transfer acid;
   the at least one transfer mechanism is to draw the transfer acid from the fluid storage and use the transfer acid to transfer the negatively-charged ions from the ion separation mechanism to the material; and
   the material is to isolate the HAA from each sample from the other ionic species from each sample as a function of a π-π bonding interaction between the HAA and the material that is dependent on the presence of the transfer acid.

3. The apparatus of claim 2, wherein the transfer acid has a pH of less than 1.0.

4. The apparatus of claim 1, wherein:
   the at least one fluid comprises a cleaning fluid; and
   the at least one transfer mechanism comprises at least one fluidic transfer mechanism to fluidically transfer each one of the samples from the intake to the ion separation mechanism and to, following transfer of the negatively-charged ions extracted from the one of the samples to the material, fluidically transfer the cleaning fluid to the ion separation mechanism to renew the ion separation mechanism for the ensuing one of the samples.

5. The apparatus of claim 1, wherein:
   the apparatus further comprises at least one processor and digital memory;
   the at least one processor is to obtain values from the measurement device in response to measurement of HAA presence in respective ones of the samples, is to compute a HAA quantity present in each respective one of the samples dependent on the corresponding value, and is to store each computed HAA quantity in the digital memory.

6. The apparatus of claim 5, wherein:
the digital memory is further to store at least one threshold;
the at least one processor is to compare at least one computed HAA quantity with the at least one threshold; and
the at least one processor is to generate a communication dependent on the comparison, to signify HAA presence greater than an associated threshold of the at least one threshold for at least one of the samples, and is to unsolicitedly convey the communication to a human operator.

7. The apparatus of claim 1, wherein:
the apparatus further comprises at least one processor and circuitry to transmit data to a predetermined destination via a wide area network connection; and
the at least one processor is to obtain values from the measurement device in response to measurement of the HAA extracted from respective ones of the samples, and is to transmit data representing each of the values to the predetermined destination via the wide area network connection.

8. The apparatus of claim 1, wherein the at least one transfer mechanism and the sample extraction mechanism comprise a common pump and a manifold fluidic selector, and wherein the pump and manifold selector are to be electronically actuated to fluidically draw each of the samples, to transfer the negatively-charged ions extracted from each sample to the material, the separated HAA from the material to the measurement device, and the at least one fluid to the ion separation mechanism and the material, so as to renew the ion separation mechanism and the material for measurement of the ensuing one of the samples.

9. The apparatus of claim 8, wherein:
the at least one fluid further comprises a HAA standard;
the apparatus is characterized by operation in a normal mode and a calibration mode;
the control device is to implement the test mode by drawing the HAA standard from the fluid storage in lieu of a sample, and by electronically actuating each of the sample extraction mechanism, the measurement device and the at least one transfer mechanism in order to cause the measurement device to measure quantity of the HAA present in the HAA standard; and
the apparatus is to receive and store at least one programmed value in response to comparison between measurement, by the measurement device, of the quantity of HAA present in the HAA standard, and at least one predetermined value.

10. The apparatus of claim 1, wherein the measurement device comprises a high performance liquid chromatography (HPLC) measurement device and a spectral photometric device that are to measure quantity of each individual HAA specie present in each of the samples.

11. The apparatus of claim 1, wherein the apparatus further comprises digital storage, and wherein the apparatus comprises at least one wide area network communication device that is to provide secure, remote access by a remote human user via a wide area network connection to data in the digital storage, said data representing measurement by the measurement device of HAA presence in the samples, subject to presentation by the remote human user of at least one secret value.

12. A method of measuring presence of a haloacetic acid ("HAA") in aqueous solution, using an ion separation mechanism, a material to separate HAA from other ionic species, and a measurement device to measure HAA presence, the method comprising:
fluidically drawing samples from a supply of the aqueous solution via an intake, each of the samples having an expected volume;
providing each of the samples to the ion separation mechanism to separate negatively charged ions from the corresponding sample, the negatively-charged ions including the HAA and the other ionic species;
transferring the negatively-charged ions to the material to separate HAA from other ionic species extracted from each sample;
transferring the separated HAA to the measurement device and using the measurement device to measure HAA presence for each associated one of the samples;
transferring a fluid to the ion separation mechanism and the material, so as to renew the ion separation mechanism and the material for measurement of an ensuing one of the samples; and
wherein drawing samples, providing each of the samples, transferring the negatively-charged ions and transferring the fluid are performed using a control device to electronically actuate each of the sample extraction mechanism, the measurement device and at least one transfer mechanism to draw each of the samples from the supply, to cause the measurement device to measure HAA extracted from each of the samples using the material and to renew the ion separation mechanism and the material using the fluid.

13. The method of claim 12, wherein:
transferring the negatively-charged ions comprises using a transfer acid to transfer the negatively-charged ions from the ion separation mechanism to the material; and
the material is to isolate the HAA from each sample from the other ionic species from each sample as a function of a π-π bonding interaction between the HAA and the material that is dependent on the presence of the transfer acid.

14. The method of claim 13, wherein the transfer acid has a pH of less than 1.0.

15. The method of claim 12, wherein the method is also to use at least one processor and digital memory, further comprising:
using the at least one processor to obtain values from the measurement device in response to measurement of HAA presence in respective ones of the samples, to compute a HAA quantity present in each respective one of the samples dependent on the corresponding value, and to store each computed HAA quantity in the digital memory.

16. The method of claim 15, wherein:
the digital memory is further to store at least one threshold;
using the at least one processor further comprises
comparing at least one computed HAA quantity with the at least one threshold,
generating a communication dependent on the comparing, to signify HAA presence greater than an associated threshold of the at least one threshold for at least one of the samples, and
unsolicitedly conveying the communication to a human operator.

17. The method of claim 12, wherein the method is further to use at least one processor and circuitry to transmit data to a predetermined destination via a wide area network connection, and wherein the method further comprises using the at least one processor to obtain values from the measurement device in response to measurement of HAA extracted from respective ones of the samples, and to transmit data representing each of the values to the predetermined destination via the wide area network connection.

18. The method of claim 12, wherein the method is further to use a common pump and a manifold fluidic selector, and wherein further comprises electronically actuating the pump and manifold selector to:

fluidically draw each of the samples from the supply, transfer the negatively-charged ions from each sample to the material, transfer the separated HAA from the material to the measurement device, and transfer the at least one fluid to the ion separation mechanism and the material, so as to renew the ion separation mechanism and the material for measurement of the ensuing one of the samples.

19. The method of claim 18, further characterized by operation in a normal mode and a calibration mode, wherein the method further comprises implementing the test mode by:

drawing the HAA standard from the fluid storage in lieu of a sample, causing the measurement device to measure quantity of the HAA present in the HAA standard, and receiving and storing at least one programmed value in response to comparison between measurement, by the measurement device, of the quantity of HAA present in the HAA standard, and at least one predetermined value.

20. The method of claim 19, wherein the measurement device comprises a high performance liquid chromatography (HPLC) measurement device and a spectral photometric device that are to measure quantity of each individual HAA specie present in each of the samples.

21. The method of claim 12, wherein the method is further to use a computer, and wherein the method further comprises providing secure, remote access by a remote human user via a wide area network connection to data stored by the computer, said data representing measurement by the measurement device of HAA presence in the samples, subject to presentation by the remote human user of at least one secret value to authenticate the remote human user as one authorized to access said data.

\* \* \* \* \*